(12) United States Patent
Manca et al.

(10) Patent No.: US 10,506,833 B2
(45) Date of Patent: Dec. 17, 2019

(54) VAPORIZER INCLUDING A HEATER ASSEMBLY AND DELIVERY DEVICE

(71) Applicant: Altria Client Services LLC, Richmond, VA (US)

(72) Inventors: Laurent Manca, Sullens (CH); Rui Nuno Batista, Morges (CH)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 16/160,160

(22) Filed: Oct. 15, 2018

(65) Prior Publication Data

US 2019/0045847 A1    Feb. 14, 2019

Related U.S. Application Data

(63) Continuation of application No. 15/475,297, filed on Mar. 31, 2017, now Pat. No. 10,098,387, which is a
(Continued)

(30) Foreign Application Priority Data

Mar. 31, 2016    (EP) .................................... 16163416

(51) Int. Cl.
*A24F 47/00*    (2006.01)
*H05B 1/02*    (2006.01)
*H05B 3/26*    (2006.01)

(52) U.S. Cl.
CPC ......... *A24F 47/008* (2013.01); *H05B 1/0244* (2013.01); *H05B 3/265* (2013.01); *H05B 2203/013* (2013.01); *H05B 2203/021* (2013.01)

(58) Field of Classification Search
CPC ... A61M 11/042; A61M 11/041; A24F 47/008
See application file for complete search history.

(56) References Cited

U.S. PATENT DOCUMENTS 5,666,977 A    9/1997 Higgins et al.
6,103,810 A    8/2000 Frayer et al.
(Continued)

FOREIGN PATENT DOCUMENTS

EP    0845220 A1    6/1998
EP    2719416 A1    4/2014
(Continued)

OTHER PUBLICATIONS www.spray.com, retrieved on Dec. 5, 2018.
(Continued)

*Primary Examiner* — Ross N Gushi
(74) *Attorney, Agent, or Firm* — Harness, Dickey & Pierce, P.L.C.

(57) ABSTRACT

A vaporizing assembly for an aerosol-generating system may comprise a delivery device and a heater assembly. The heater assembly may comprise a heat resistive substrate and a heating element. The delivery device is configured to deliver an aerosol-forming substrate to at least a surface of the heat resistive substrate, wherein the heating element is isolated or separated from the aerosol-forming substrate by the heat resistive substrate. The present disclosure is also directed to a method for generating an aerosol.

19 Claims, 3 Drawing Sheets

Related U.S. Application Data continuation of application No. PCT/EP2017/056741, filed on Mar. 21, 2017.

(56) References Cited

U.S. PATENT DOCUMENTS

| | | | |
|---|---|---|---|
| 9,439,455 | B2 | 9/2016 | Alarcon et al. |
| 9,538,788 | B2 * | 1/2017 | Cyphert ............... A24F 47/008 |
| 2008/0023003 | A1 | 1/2008 | Rosenthal |
| 2014/0144429 | A1 | 5/2014 | Wensley et al. |
| 2015/0276262 | A1 | 10/2015 | Dai et al. |
| 2017/0196266 | A1 | 7/2017 | Chen |
| 2017/0265523 | A1 | 9/2017 | Lipowicz |

FOREIGN PATENT DOCUMENTS

| WO | WO-00/21598 A1 | 4/2000 |
|---|---|---|
| WO | WO-2004/022128 A2 | 3/2004 |
| WO | WO-2016/005530 A1 | 1/2016 |
| WO | WO-2016/005531 A1 | 1/2016 |
| WO | WO-2016/005533 A1 | 1/2016 |
| WO | WO-2016/005600 A1 | 1/2016 |
| WO | WO-2016/005601 A1 | 1/2016 |
| WO | WO-2016/005602 A1 | 1/2016 |
| WO | WO-2016/033242 A1 | 3/2016 |

OTHER PUBLICATIONS www.leeproducts.co.uk, retrieved on Dec. 5, 2018.
http://www.morphyrichardsredefine.com/, retrieved on Dec. 5, 2018.
http://www.industrial-microhydraulics.co.uk/check_valves.htm, retrieved on Dec. 5, 2018.
Extended European Search Report dated Jul. 15, 2016 for corresponding European Application No. 16163416.7.
International Preliminary Report on Patentability dated Oct. 11, 2018 for corresponding International Application No. PCT/EP2017/056741.
International Search Report and Written Opinion thereof dated Jun. 14, 2017 for corresponding International Application No. PCT/EP2017/056741.

* cited by examiner

VAPORIZER INCLUDING A HEATER ASSEMBLY AND DELIVERY DEVICE

CROSS-REFERENCE TO RELATED APPLICATIONS

This application is a continuation under 35 U.S.C. § 120 of U.S. application Ser. No. 15/475,297, filed Mar. 31, 2017, which claims priority to PCT/EP2017/056741, filed on Mar. 21, 2017, and further claims priority to EP 16163416.7, filed on Mar. 31, 2016, the entire contents of each of which are incorporated herein by reference.

BACKGROUND

Field

Example embodiments relate to a vaporizing assembly for an aerosol-generating system (e.g., a handheld electrically operated aerosol-generating system).

Description of Related Art

There are handheld electrically operated aerosol-generating systems that consist of a device portion comprising a battery and control electronics, a cartridge portion comprising a supply of aerosol-forming substrate held in a liquid storage portion, and an electrically operated vaporizer. The vaporizer typically comprises a coil of heater wire wound around an elongate wick soaked in the liquid aerosol-forming substrate held in the liquid storage portion. The cartridge portion typically comprises not only the supply of aerosol-forming substrate and an electrically operated vaporizer but also a mouthpiece from which the aerosol exits.

In aerosol-generating systems, the liquid aerosol-generating medium may not always be completely volatilized. Residues may be created upon transport and heating of the liquid aerosol-forming substrate. Such residues may affect aerosol creation. In particular, residues may impair repeatability of aerosol creation.

In aerosol-generating systems, the vaporizer is usually not easily accessible and the heating elements are mostly relatively small and fragile. Thus, in these systems, cleaning of the vaporizer is relatively difficult or not possible at all.

SUMMARY

According to some example embodiments, there is provided a vaporizing assembly for an aerosol-generating system, comprising a delivery device (e.g., a liquid aerosol-forming substrate delivery device) for delivering an aerosol-forming substrate (e.g., a liquid aerosol-forming substrate), and a heater assembly. The heater assembly comprises a heat resistive substrate and a heating element. The liquid aerosol-forming substrate delivery device may be configured to deliver a liquid aerosol-forming substrate to at least a surface of the heater assembly, wherein the heating element is isolated or separated from the liquid aerosol-forming substrate during normal use.

The heat resistive substrate of the heater assembly may be transparent or semi-transparent. The heat resistive substrate of the heater assembly may be made from glass, heat resistive glass, ceramics, silicon, semiconductors, metals, or metal alloys.

The heat resistive substrate may be produced from pure glass or a glass compound, as well as glass with specific crystal orientation to enable optimized thermal transfer effects.

By forming the heater assembly from transparent or semi-transparent materials, a visual check and assessment of the need to clean the surface of the heat resistive substrate may be performed with relative ease. In order to clean the surface, the heater assembly may be rinsed with water or a suitable cleaning liquid.

The heat resistive substrate may be substantially flat and may have any desired shape. The heat resistive substrate may have a rectangular, polygonal, circular or oval shape with, for example, width and length dimensions of between 3 to 10 millimeters. The thickness of the heat resistive substrate may range between 0.2 and 2.5 millimeters. In some example embodiments, the heat resistive substrate may be have a rectangular shape with a size of about 7×6 millimeters or 5×5 millimeters (L×W), and a thickness of about 1 to 1.5 millimeters.

As used herein, "substantially flat" means an arrangement that is in the form of a substantially two dimensional object. Thus, the substantially flat heat resistive substrate extends in two dimensions substantially more than in a third dimension. In particular, the dimensions of the substantially flat heat resistive substrate in each of the two dimensions is at least 5 times larger than in the third dimension. The two dimensions may define a surface of the heat resistive substrate and third dimension may define a thickness of the heat resistive substrate, normal to the surface. An example of a substantially flat heat resistive substrate is an object between two imaginary and substantially parallel planar surfaces, wherein the distance between the two imaginary surfaces is substantially smaller than the extent of the object parallel to the surfaces. As described above, the extent of the object in two orthogonal directions parallel to the surfaces may be at least five times greater than the distance (or thickness) between the two parallel surfaces. In some example embodiments, the substantially flat heat resistive substrate is planar and the distance between the parallel planar surfaces would be the thickness of the material used for forming the heater. In other example embodiments, the substantially flat heat resistive substrate is curved along one or more dimensions, for example forming a dome shape or bridge shape.

The heating element may be transparent but may also include partially transparent or not transparent materials. For example, the heating element may comprise metallic layers or elements in at least one of the surfaces of the heat resistive substrate for the purpose of creating a resistive element. Furthermore, contact pads for electrical conductivity and connections with other parts of the device may be provided, which are not transparent. The non-transparent parts are used only in such extent so as to not hinder the ability to see and assess the need to clean the surface of the heat resistive substrate.

The heating element is isolated from the liquid aerosol-forming substrate during normal use. The expression "isolated from the liquid aerosol-forming substrate" as used throughout this application is to be understood in the sense that the heating element is provided such that it does not come into direct contact with the liquid aerosol-forming substrate during normal use. For example, as disclosed in more detail below, the heating element may be provided within the volume of the heat resistive substrate, may be sandwiched between two elements of the heat resistive substrate or may be covered with a protective layer of heat resistive material. With such configuration, contact between the heating element and the liquid aerosol-forming substrate may be completely avoided.

The expression "isolated from the liquid aerosol-forming substrate" is also to be construed in a way that it encompasses example embodiments in which the heating element is provided on a surface of the heat resistive substrate onto which the liquid aerosol-forming substrate is not directly delivered. In some example embodiments the liquid aerosol-forming substrate may be delivered to a front side of the heat resistive substrate and the heating element may be provided on a backside of the heat resistive substrate.

In such configurations, indirect contact between the heating element and the liquid aerosol-forming substrate might not be avoided. Such indirect contact may occur when residual liquid aerosol-forming substrate creeps over the heat resistive substrate or when vaporized liquid substrate condenses at the heating element.

The heating element may be provided as a thin film coating provided to the surface of the heat resistive substrate. The heating element can be impregnated, deposited, or printed on the surface of the heat resistive substrate. The material of the thin film heating element can be any suitable material which has adequate electrical properties and a sufficiently high adherence to the heat resistive substrate.

In order to allow for a homogenous heating of the heat resistive substrate, the thin film coating of the heating element may extend substantially over the complete surface of the heat resistive substrate. The geometrical shape of the heating element may vary, being any adequate shape to produce the intended electrical resistance and the intended heating capabilities.

The heating element assembly may be localized in such configuration in the vaporizing assembly that one of the large surfaces of the heat resistive substrate, also referred to as the front side (or front surface), faces towards the delivery device. In use, the liquid aerosol-forming substrate is substantially dispensed only onto the front side (or front surface) of the heat resistive substrate.

The heating element is provided to the large surface of the heat resistive substrate which points or faces away from the delivery device. This surface is also referred to as the backside of the heat resistive substrate. The backside does not come into direct contact with the liquid aerosol-forming substrate during normal operation.

The heating element is configured such that the front side of the heat resistive substrate is heated to temperatures of about between 120 degrees Celsius and 250 degrees Celsius. The actual temperature of the heater assembly may be adjusted or chosen, for example, depending on the type of liquid aerosol-forming substrate that is used.

The heating element may be embedded in the heat resistive substrate. The expression "embedded" as used throughout this application is to be understood in the sense that the heating element is provided within the volume of the heat resistive substrate, is sandwiched between two elements of the heat resistive substrate or is sandwiched between one of the surfaces of the heat resistive substrate and an additional cover layer. The cover layer may be a specific coating of glass or mainly polymeric transparent material with good resistance to temperatures up to the operating temperature of the heating element. The heating element may comprise a metallic wire which is embedded in a heat resistive substrate of glass or any other suitable material.

The heat resistive substrate of the heater assembly may be made from a material having low adhesion or anti-adhesion properties with respect to the liquid aerosol-forming substrate. This can reduce the probability of accumulation of residues on the surface of the heating element. Moreover, the heating element may be easier to clean. The surface of the heat resistive substrate of the heater assembly may be non-porous. Non-porous means that the surface of the heat resistive substrate does not allow liquid or air to pass through it.

The heater assembly may additionally comprise further sensors or components for specific additional purposes. Such additional sensors may include real-time chemical sensors and temperature sensors. With these sensors, the chemical composition and the temperature on the surface of the heater assembly can be monitored in a fast and geometrically precise way.

The heater assembly element may be an all-in-one built-in component such as a semiconductor component, a microchip component or a set of those components, manufactured using semiconductor technologies as a single component comprising nano-sized integrated structures. Such heater assemblies may be more easily connected and disconnected from the man body of the device, and are therefore desirable as replacement parts. However, depending on the material used, specific cleaning procedures may apply.

According to an example embodiment, during vaporization, the liquid aerosol-forming substrate only comes into contact with the front side (or front surface) of the heat resistive substrate.

The liquid aerosol-forming substrate delivery device is connectable to a liquid storage portion and is configured to convey the liquid aerosol-forming substrate onto the heater assembly. The liquid aerosol-forming substrate delivery device may comprise an outlet end for discharging the liquid aerosol-forming substrate onto the heater assembly. The outlet end of the delivery device may be spaced apart from the heater assembly. The distance between the outlet end of the delivery device and the heater assembly may be between 0.1 and 10 millimeters. For instance, the distance between the outlet end of the delivery device and the heater assembly may be between 0.5 and 5 millimeters (e.g., between 0.7 and 2.5 millimeters).

Example embodiments in which the heater assembly is spaced apart from delivery device may offer additional advantages. For instance, the reflux of liquid aerosol-forming substrate from the heating element to the delivery device may be efficiently prevented. Moreover, as the heating element is mechanically decoupled from the delivery device, the handling of the vaporizing assembly, in particular disassembly for replacement purposes or cleaning, is facilitated. The heater assembly may be releasably connected to the liquid aerosol-forming substrate delivery device. Releasably connected in this context means that the heater assembly may be disconnected from the liquid aerosol-forming substrate delivery device and reconnected to liquid aerosol-forming substrate delivery device without damaging either the heater assembly or liquid aerosol-forming substrate delivery device.

The delivery device may further comprise a pump for delivering the liquid aerosol-forming substrate onto the heater assembly. The pump may be a hand-operated, manual pump, an electromechanical pump, or a micropump.

Micropumps may allow on-demand delivery of liquid aerosol-forming substrate at a low flow rate of for example approximately 0.5 to 4.5 microliters per second for intervals of variable or constant duration. The pump may be tuned in order to deliver the appropriate amount of liquid aerosol-forming substrate to the heating element. Consequently, the amount of deposited liquid aerosol-forming substrate can be determined from the amount of pump cycles.

The pumped volume of one complete cycle of a micropump typically is about 0.50 microliters per second. Such micropumps typically are operated at a pump frequency of between 5 to 20 hertz.

The pump may be configured to pump liquid aerosol-forming substrates that are characterized by a relatively high viscosity as compared to water. The viscosity of a liquid aerosol-forming substrate may be in the range from about 10 to 500 millipascal seconds (e.g., in the range from about 17 to 86 millipascal seconds).

The liquid aerosol-forming delivery device may further be configured to deliver a metered amount of liquid aerosol-forming substrate onto the heater assembly. The estimated maximum amount of liquid to be pumped as a dose for a puff is a small volume, as a pumping pulse liquid volume from 0.010 to 0.060 microliters (e.g., around 0.0125 microliters).

At the outlet end of the liquid aerosol-forming substrate delivery device a nozzle may be provided via which the liquid aerosol-forming substrate may be sprayed onto the heater assembly for volatilization and aerosol creation. The nozzle converts the flow of the liquid aerosol-forming substrate into a plurality of small droplets. The spray pattern of the droplets may be adapted to the shape of the heater assembly.

The delivery device may comprise a classic type atomizer spray nozzle, in which case a flow of air is supplied through the nozzle upon an application of negative pressure, creating a pressurized air flow that will mix and act with the liquid creating an atomized spray in the outlet of the nozzle. Several systems are available on the market including nozzles that work with small volumes of liquid, in sizes that meet the requirements to fit in small portable devices. Another class of nozzle that may be used is an airless spray nozzle, sometimes referred to as a micro-spray nozzle. Such nozzles create micro spray cones in very small sizes. With this class of nozzles, the airflow management inside the device, namely inside the mouthpiece, surrounds the nozzle and the heater assembly, flushing the heater assembly surface towards the outlet of the mouthpiece (e.g., including a turbulent air flow pattern of the aerosol exiting the mouthpiece).

For either class of nozzle, the distance of the air gap between the delivery device and the surface of the heat resistive substrate facing the nozzle, may be within a range from 2 to 10 millimeters (e.g., from 3 to 7 millimeters). Any type of available spraying nozzles may be used. Airless nozzle 062 Minstac from manufacturer "The Lee Company" is an example of a suitable spray nozzle.

The vaporizing assembly may have a longitudinal axis. The delivery device may deliver or spray liquid aerosol-forming substrate along the longitudinal axis. The heat resistive substrate may have a surface that receives the liquid aerosol-forming substrate and the surface may be oblique to the longitudinal axis of the vaporizing assembly (e.g., so as to form an obtuse angle). In the case of a non-planar surface of the heat resistive substrate, the surface of at least a central portion of the heater assembly that receives liquid aerosol-forming substrate from the delivery device delivered along the longitudinal axis may be oblique to the longitudinal axis of the vaporizing assembly.

A coupling unit may be provided in order to connect the delivery device to a liquid storage portion. The coupling unit may include a "luer" type connection. However, any type of leakage free connection system may be used.

According to some example embodiments, there is provided an aerosol-generating system comprising a vaporizing assembly as disclosed above and a housing in which the vaporizing assembly is located. At least a part of the housing in which the heater assembly of the vaporizing assembly is located, is made from transparent material, such that the heater assembly can be visually inspected.

The housing of the aerosol-generating system may comprise a mouthpiece through which the generated aerosol exits. The mouthpiece may be detachably connected to the housing. The heater assembly of the vaporizing assembly may be located in the mouthpiece. At least a portion of the mouthpiece may be transparent, such that the heater assembly can be visually inspected.

The transparent portion of the housing or the mouthpiece may be made from for example thermal resistant glass, shock resistant glass, polymeric materials, hybrid compounds, carbon compounds, graphite, polysulfone (PSU), polyethersulfone (PES), or polyphenylsulfone (PPSU).

The mouthpiece and the heater assembly may be integrally formed as a single part. The mouthpiece and the heater assembly may be provided as a replaceable part, which can be changed after use.

The heater assembly of the aerosol-generating system can be visually inspected with relative ease. When undesired contaminations are detected, the aerosol-generating system may be disassembled, and the heater assembly may be cleaned. The design of the vaporizing assembly allows the cleaning of the heating element with relative ease, for example by rinsing with water.

The aerosol-generating system may further comprise a device portion including a power supply and a control unit. The aerosol-generating system may further comprise a replaceable liquid storage portion. When assembled, the liquid storage portion is in fluid connection with the liquid aerosol-forming substrate delivery device. The mouthpiece may be detachable from the device portion and the liquid storage portion.

In some example embodiments, the liquid storage portion may comprise pressurized liquid. The liquid may be stored in the liquid storage portion in a collapsible balloon. A one way valve may be temporarily opened to allow liquid flow out of the liquid storage portion.

In some example embodiments, the liquid storage portion may have a flexible or movable wall. By manual or electromechanical action onto the moveable wall, the liquid aerosol-forming substrate may be forced out of the liquid storage portion. The liquid aerosol-forming substrate from the liquid storage portion may then be delivered by the delivery device to the heater assembly.

Additional one-way valves may be provided in the delivery device wherever it is desired to avoid reflux of the liquid aerosol-forming substrate. To this end, commercially available one-way valves with adequate size and liquid flows may be used, including mini and micro flutter valves, duckbill valves, check valves. The valves may be made of materials resistant to aggressive chemicals or FDA certified materials, which may be used for food industry and medical applications.

The aerosol-generating system may further comprise a control unit connected to the vaporizer and to an electrical power source.

The control unit may be used to set the temperature and the heating duration of the heating element. The control unit may also be used to activate the pump in order to deliver the liquid aerosol-generating substrate onto the heater assembly. To this end the control unit may be in communication with an air flow sensor, which allows the control unit to detect the application of a negative pressure.

The control unit may comprise a microprocessor, which may be a programmable microprocessor. The control unit may comprise further electronic components. The control unit may be configured to regulate a supply of power to the vaporizing assembly. Power may be supplied to the vaporizing assembly continuously following activation of the system or may be supplied intermittently, such as on a puff-by-puff basis. The power may be supplied to the vaporizing assembly in the form of pulses of electrical current.

The power supply provides the required electric energy to the electric components of the aerosol-generating system. The power supply may be in form of a charge storage device such as a capacitor. The power supply may require recharging and may have a capacity that allows for the storage of enough energy for one or more periods of aerosol generation. For example, the power supply may have sufficient capacity to allow for the continuous generation of aerosol for a period of around six minutes or for a period that is a multiple of six minutes. In another example, the power supply may have sufficient capacity to allow for a predetermined or target number of puffs or discrete activations of the heater assembly.

For allowing air to enter the aerosol-generating system, a wall of the housing of the aerosol-generating system is provided with at least one semi-open inlet. In an example embodiment, the semi-open inlet allows air to enter the aerosol-generating system, but no air or liquid to leave the aerosol-generating system through the semi-open inlet. A semi-open inlet may, for example, be a semi-permeable membrane, permeable in one direction only for air, but is air- and liquid-tight in the opposite direction. A semi-open inlet may for example also be a one-way valve. Preferably, the semi-open inlets allow air to pass through the inlet only if specific conditions are met, for example a minimum depression in the aerosol-generating system or a volume of air passing through the valve or membrane.

The liquid aerosol-forming substrate is a substrate capable of releasing volatile compounds that can form an aerosol. The volatile compounds may be released by heating the liquid aerosol-forming substrate. The liquid aerosol-forming substrate may comprise plant-based material. The liquid aerosol-forming substrate may comprise tobacco. The liquid aerosol-forming substrate may comprise a tobacco-containing material containing volatile tobacco flavour compounds, which are released from the liquid aerosol-forming substrate upon heating. The liquid aerosol-forming substrate may alternatively comprise a non-tobacco-containing material. The liquid aerosol-forming substrate may comprise homogenised plant-based material. The liquid aerosol-forming substrate may comprise homogenised tobacco material. The liquid aerosol-forming substrate may comprise at least one aerosol-former. The liquid aerosol-forming substrate may comprise other additives and ingredients, such as flavourants.

The aerosol-generating system may be an electrically operated aerosol-generating system. Preferably, the aerosol-generating system is portable. The aerosol-generating system may have a size comparable to a cigar or cigarette. The aerosol-generating system may have a total length between approximately 30 millimeters and approximately 150 millimeters. The aerosol-generating system may have an external diameter between approximately 5 millimeters and approximately 30 millimeters.

The aerosol-generating system may be elongate and have a longitudinal axis. An outlet may be provided in the mouthpiece at one end of the longitudinal axis. The surface of the heat resistive substrate may be oblique to the longitudinal axis of the aerosol-generating system. This may improve the transport of vapour and liquid from the heater assembly to the outlet. In the case of a non-planar surface of the heat resistive substrate, the surface of at least a central portion of the heater assembly may be oblique to the longitudinal axis of the aerosol-generating system.

According to some example embodiments, there is provided a method for generating aerosol, comprising the steps of storing liquid aerosol-forming substrate in a liquid storage portion, providing a heater assembly comprising a heat resistive substrate and an electric heating element, delivering liquid aerosol-forming substrate from the liquid storage portion to the heater assembly via a delivery device, and volatilizing at least a part of the delivered liquid aerosol-forming substrate by activating the heating element of the heater assembly. The heating element is isolated from the liquid aerosol-forming substrate. The heating element therefore does not directly contact the liquid aerosol-forming substrate in normal use.

Direct contact between the liquid aerosol-forming substrate and the heating element may be avoided by embedding the heating element in the heat resistive substrate of the heater assembly or by providing the heating element on a surface of the heat resistive substrate which does not come into contact with the liquid aerosol-forming substrate.

The method may further comprise the step of providing a housing in which the heater assembly is located, wherein at least the part of the housing in which the heater assembly is located, is made from transparent material, such that the heater assembly can be visually inspected from outside. This allows the verification of whether contaminations or residues have formed on the heater assembly. In case such undesired contaminations have indeed formed, the appropriate steps can be taken to remove these contaminations. In order to facilitate maintenance of the aerosol-generating system, the mouthpiece including the heater assembly is configured to be cleanable, for example rinseable with water.

During normal operation of the aerosol-generating system, the delivery of the liquid aerosol-forming substrate and the heating element may be triggered by a puff detection system. Alternatively, these elements may be triggered by pressing an on-off button, held for the duration of a puff.

In some example embodiments, the delivery of the liquid aerosol-forming substrate may be delayed to the activation of the heating element. In these embodiments the heating element is pre-heated to a desired operation temperature, before the liquid aerosol-forming substrate is delivered onto the heater assembly.

It should be understood that features described in relation to one or more examples may equally be applied to other examples.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
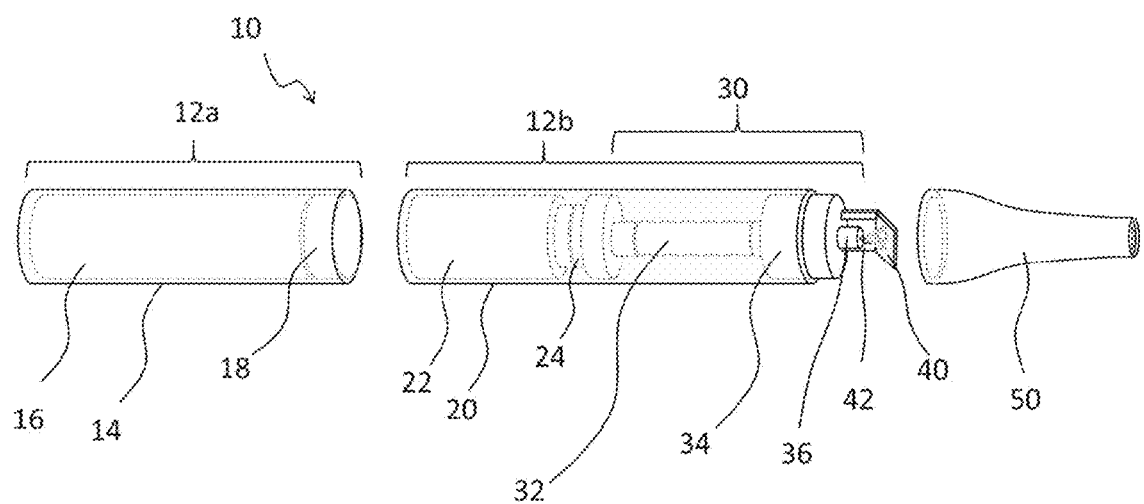
FIG. 1 is an exploded view of an aerosol-generating system according to an example embodiment.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1 is an exploded view of the components of an aerosol-generating system according to an example embodiment. Referring to FIG. 1, the aerosol-generating system 10 comprises a device portion 12a including a housing 14, a power source 16, and a control unit 18. The aerosol-generating system 10 further comprises a vaporizer assembly 12b including a housing 20, a storage portion 22 (e.g., exchangeable liquid storage portion), a delivery device 30, and a heater assembly 40. A transparent mouthpiece 50 can be detachably connected to the housing 20 of the vaporizer assembly 12b.

The device portion 12a and the vaporizer assembly 12b may be connected via any suitable coupling unit which provides an adequate mechanical and electrical connection between the device portion 12a and the vaporizer assembly 12b.

The liquid storage portion 22 is connected to the aerosol-forming substrate delivery device 30 via a coupling unit 24. In an example embodiment, the coupling unit 24 is a "luer" type coupling unit. The liquid storage portion 22 can be replaced with relative ease by separating the vaporizer assembly 12b from the device portion 12a and removing the liquid storage portion 22 from the open distal end of the vaporizer assembly 12b.

In an example embodiment, the liquid aerosol-forming substrate delivery device 30 is configured to transport the liquid aerosol-forming substrate from the liquid storage portion 22 to the heater assembly 40. To achieve this transport, the liquid aerosol-forming substrate delivery device 30 may comprise a tubing 32 and a micropump 34 which are in fluidic connection with the liquid storage portion 22. The micropump 34 is configured to pump the liquid aerosol-forming substrate to the heater assembly 40.

At the outlet end of the liquid aerosol-forming substrate delivery device 30, a spray nozzle 36 may be provided. The spray nozzle 36 is configured to dispense the liquid aerosol-forming substrate to the heater assembly 40 in a predetermined or target spray pattern. In an example embodiment, the nozzle 36 is an airless nozzle that provides a cone-like spray pattern. The spray pattern may be adapted to the size of the surface of the heater assembly 40.

The heater assembly 40 may comprise a substantially rectangular substrate 42 made from thermo-resistive glass. The substrate 42 may have a size of 5×5 square millimetres and a thickness of 1 millimeter. In an example embodiment, the substrate 42 is mounted on support posts 44, which in turn are fixed to the housing 20 of the vaporizer assembly 12b. The substrate 42 may be mounted such that its front side 42a faces the nozzle 36 and is held at a distance of about 7 millimetres from the nozzle 36. The front side 42a of the substrate 42 may be at an oblique angle (e.g., obtuse angle) to the longitudinal axis of the aerosol-generating system 10. This configuration improves the transport of liquid droplet and vapour from the substrate 42 through the mouthpiece 50 when compared to an arrangement in which the front side 42a of the substrate 42 is perpendicular to the longitudinal axis of the aerosol-generating system 10.

The heater assembly 40 further comprises a heating element 46, which may be in the form of a conductive thin film coating that is applied to the backside 42b of the substrate 42. The thin film coating may be electrically connected via the support posts 44 to the control unit 18 and the power source 16 of the device portion 12a. The support posts 44 may also provide electrical contacts for establishing the electrical connection between the heater assembly 40 and the power source 16. When the heating element 46 is provided on the backside 42b of the substrate 42, the heating element 46 does not come into direct contact with the liquid aerosol-forming substrate under normal operating conditions.

The micropump 34 is electrically connected with the power source 16 and controlled by the control unit 18. The micropump 34 can be activated to provide a desired liquid flow through the nozzle 36 provided at the outlet end of the liquid aerosol-forming substrate delivery device 30.

By applying an electrical current to the thin film coating, the heat resistive substrate 42 is heated up to temperatures of above 120° Celsius, which is sufficient to volatilize the liquid aerosol-forming substrate sprayed on the front side 42a of the heat resistive substrate 42.

Figure 2:
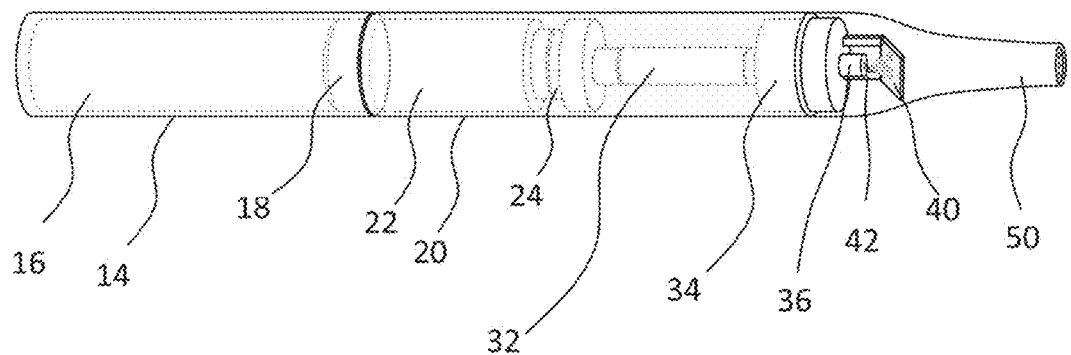
FIG. 2 is an assembled view of the aerosol-generating system of FIG. 1.

In FIG. 2, the aerosol-generating system 10 is depicted in a fully assembled state. In an example embodiment, the entire mouthpiece 50 may be made from shock resistant transparent glass. Due to the transparency of the mouthpiece 50 and the heater assembly 40, the aerosol-formation in the aerosol-generating system 10 and the cleanliness of the vaporization unit can be visually monitored.

The aerosol-generating system 10 may be activated by a manual operation of a power switch or may automatically be activated by corresponding detection means upon the application of a negative pressure. Upon detection of such signals, the heater assembly 40 and the liquid aerosol-forming substrate delivery device 30 are activated by the control unit 18. The liquid aerosol-forming substrate delivered to the heater assembly 40 is vaporized and is mixed with the air stream to form an aerosol.

The specific design of the aerosol-generating system 10 ensures that the delivered liquid aerosol-forming substrate is substantially (or completely) volatilized and that the formation of residues within the inner surface of the mouthpiece 50 and on the heater assembly 40 is reduced or avoided. Due to the transparency of the employed materials, a verification that no undesired residues have formed can be performed at any time. Should such undesired residues form, the aerosol-generating system 10 allows for relatively easy access to internal parts of the system. By removing the detachable mouthpiece 50, access to the heater assembly 40 may be gained in order to rinse the mouthpiece 50 and the heater assembly 40 (e.g., with tap water or any other suitable cleaning liquid).

Figure 3:
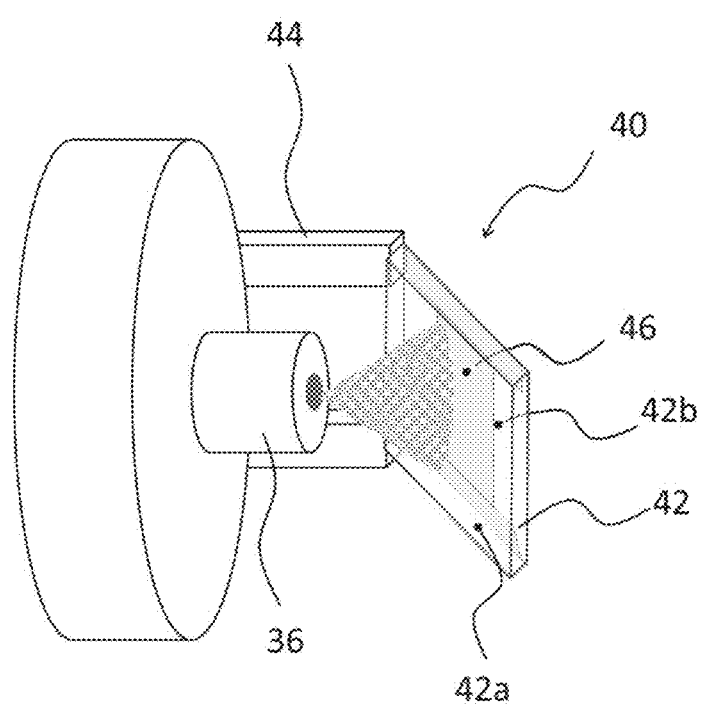
FIG. 3 is an enlarged view of the heater assembly of FIG. 1.

FIG. 3 shows an enlarged view of the heater assembly 40. Referring to FIG. 3, the heat resistive substrate 42 is mounted on support posts 44 and is held at a predefined or desired distance from the nozzle 36. The front side 42a of the heat resistive substrate 42 faces towards nozzle 36, such that the liquid aerosol-forming substrate is directly delivered only onto the front side 42a of the heat resistive substrate 42. The backside 42b of the heat resistive substrate 42 may be provided with a heating element 46 in the form of an electrically conductive thin film coating. The support posts 44 are also used for electrically contacting the conductive thin film coating to the power source 16 of the aerosol-generating system 10. In an example embodiment where the heating element 46 is provided on the backside 42b of the heat resistive substrate 42, the heating element 46 does not come into direct contact with the liquid aerosol-forming substrate delivered via nozzle 36. The heater assembly 40 may be detachable from the nozzle 36 to allow for removal and cleaning. The support posts 44 may be received in slots in the nozzle 36. The heater assembly 40 may be fixed to the mouthpiece 50.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A vaporizer comprising:
    a heater assembly including a substrate and a heating element, the substrate including a first surface and an opposing second surface, the heating element disposed on the second surface of the substrate; and
    a delivery device spaced apart from the heater assembly, the delivery device configured to dispense a liquid onto the first surface of the substrate, the heating element disposed such that the first surface of the substrate is between the delivery device and the heating element.

2. The vaporizer of claim 1, wherein the substrate of the heater assembly is at an angle to a longitudinal axis of the vaporizer.

3. The vaporizer of claim 1, wherein the substrate of the heater assembly is transparent or semi-transparent.

4. The vaporizer according to claim 1, wherein the substrate of the heater assembly is non-porous.

5. The vaporizer of claim 1, wherein the first surface of the substrate is planar.

6. The vaporizer of claim 1, wherein the heating element is configured to heat the first surface of the substrate to vaporize the liquid.

7. The vaporizer of claim 1, wherein the heating element is downstream from the delivery device.

8. The vaporizer of claim 1, wherein the heating element is in a form of a film.

9. The vaporizer according to claim 1, wherein the heater assembly is configured such that the heating element does not come into direct contact with the liquid during a normal operation of the vaporizer.

10. The vaporizer of claim 1, wherein the heating element is sandwiched between the substrate and an adjacent layer.

11. The vaporizer according to claim 1, wherein the heater assembly is releasably connected to the delivery device.

12. The vaporizer according to claim 1, wherein the delivery device includes an outlet end spaced 0.1 mm to 10 mm from the heater assembly.

13. The vaporizer according to claim 1, wherein the delivery device is configured to dispense a metered amount of the liquid.

14. The vaporizer according to claim 13, wherein the metered amount is 0.01 to 0.06 microliters.

15. The vaporizer according to claim 1, wherein the substrate of the heater assembly is spaced apart from the delivery device by a support post.

16. The vaporizer according to claim 1, wherein the delivery device has a longitudinal axis and is configured to dispense the liquid in a direction coinciding with the longitudinal axis.

17. The vaporizer according to claim 1, wherein the delivery device has a longitudinal axis, and the first surface of the substrate is at an oblique angle to the longitudinal axis.

18. A vaporizer comprising:
a heater assembly including a substrate and a heating element, the substrate including a first surface and an opposing second surface; and
a delivery device spaced apart from the heater assembly, the delivery device configured to dispense a liquid onto the first surface of the substrate, the heating element disposed such that the first surface of the substrate is between the delivery device and the heating element,
wherein the heating element is embedded within the substrate.

19. A vaporizer comprising:
a heater assembly including a substrate and a heating element, the substrate including a first surface and an opposing second surface; and
a delivery device spaced apart from the heater assembly, the delivery device configured to dispense a liquid onto the first surface of the substrate, the heating element disposed such that the first surface of the substrate is between the delivery device and the heating element,
wherein the delivery device includes a pump and a nozzle configured to spray the liquid.

* * * * *